United States Patent [19]

Watanabe et al.

[11] Patent Number: 5,288,374
[45] Date of Patent: Feb. 22, 1994

[54] METHOD AND APPARATUS FOR ELECTROCHEMICAL ANALYSIS AND AN AQUEOUS SOLUTION FOR USE THEREIN

[75] Inventors: Miyoko Watanabe; Hiroshi Mitsumaki, both of Mito, Japan

[73] Assignee: Hitachi, Ltd., Tokyo, Japan

[21] Appl. No.: 580,121

[22] Filed: Sep. 10, 1990

[30] Foreign Application Priority Data

Sep. 13, 1989 [JP] Japan .................................. 1-238242

[51] Int. Cl.⁵ ............................................ G01N 27/30
[52] U.S. Cl. .................... 204/153.1; 204/409; 204/412; 204/415
[58] Field of Search ............ 204/153.1, 153.14, 153.15, 204/153.17, 402, 403, 409, 412, 415

[56] References Cited

U.S. PATENT DOCUMENTS

| | | | |
|---|---|---|---|
| 3,556,950 | 1/1971 | Dahms | 204/409 X |
| 4,409,088 | 10/1983 | Kanno et al. | 204/409 X |
| 4,680,270 | 7/1987 | Mitsumaki et al. | |
| 4,797,191 | 1/1989 | Metzner et al. | 204/409 X |
| 4,995,959 | 2/1991 | Metzner | 204/409 X |

FOREIGN PATENT DOCUMENTS 60-73359  4/1985  Japan .

OTHER PUBLICATIONS

"TBS-50S Development of Urine Measuring System", Japanese Journal of Clinical Laboratory Automation, 12(4), p. 78, 1987.

*Primary Examiner*—Nam Nguyen
*Attorney, Agent, or Firm*—Fay, Sharpe, Beall, Fagan, Minnich & McKee

[57] ABSTRACT

A method of electrochemical analysis involves contacting fluid samples of first and second different types in a mixed sequence with an electrochemical sensor, and also contacting the sensor with a standard fluid, in order to measure the values of an analytical item, e.g. ionic activity, in the samples with reference to a standard value of the same analytical item in the standard fluid. To improve response of the sensor, at each change in the sequence from the first sample type to the second sample type, the sensor is contacted with a second fluid having a value of the analytical item closer to the mean value of the analytical item in the second sample type than the value of the analytical item in the standard fluid. The method is applicable for example to analysis of blood serum and urine using an ion selective electrode.

15 Claims, 5 Drawing Sheets

METHOD AND APPARATUS FOR ELECTROCHEMICAL ANALYSIS AND AN AQUEOUS SOLUTION FOR USE THEREIN

BACKGROUND OF THE INVENTION

1. Field of the Invention

This invention relates to a method and apparatus for electrochemical analysis of fluid samples, and also to an aqueous solution useful in such method and apparatus. The invention is especially applicable in the medical field, but is not limited thereto. The invention will be described below particularly in relation to the analysis of blood serum and urine samples, but is applicable to the analysis of a wide variety of other samples.

2. Description of the Related Art

In electrochemical analysis, the response time of an electrochemical sensor in which ion transport takes place is often relatively slow. It is generally sought to improve the response time and thus the sensitivity of the sensor. One known form of sensor is the ion selective electrode in which a sample to be measured contacts an ion selective membrane containing ligands which specifically transport the ion being measured. An internal solution of the electrode, which typically contains an electrolyte of the gel type, also contains the ion being measured. An electromotive force (emf) is generated in the cell as a result of the concentration gradient across the ion selective membrane, and this emf is measured in order to measure the concentration of the selected ion in the sample solution. Strictly speaking, it is the ionic activity in the sample solution which is measured, not the concentration, but the two are related.

Such ion selective electrodes are used for example in blood serum analyzers. Typically, the prepared sample of blood serum is passed consecutively through three ion selective electrodes, which measure the concentrations of sodium ions, potassium ions and chloride ions in the sample. Such analyzers are nowadays large machines which perform a large number of other analytical measurements on blood samples. For convenience, for example in a hospital, it is also desired to analyze urine samples in the same machine, in particular to measure the concentration of sodium, potassium and chloride ions in a urine sample using the same ion selective electrodes. The problem arises that while the characteristics of samples derived from blood, e.g. serum or plasma, are generally similar, the characteristics of urine in relation to the ion selective electrode are very different from those of samples derived from blood. Because the ion selective electrode has a relatively long response time, its response to a urine sample can be unacceptably slow.

One solution to this problem is to batch the samples, so that urine samples are presented to the ion selective electrodes separately from samples derived from blood. However, this is inconvenient for the operator of the machine, when presented with a large number of samples which arrive for analysis in a random order, or when a particular sample must be analysed urgently.

A further problem in the prior art can be the frequent need to perform a priming operation, i.e. to fill the whole flow passage of the apparatus with a diluting solution, e.g. to put it into a uniform condition. This takes time and consumes diluting solution. Particularly, if samples are batched according to type, priming after each batch is thought necessary.

One known form of blood analysis machine is the "TBA-50S" of Toshiba. To enable serum samples and urine samples in a random order, this machine is arranged to dilute urine samples preliminarily and for this purpose a special dilution line is added. See "TBA-50S Development of Urine Measuring System", Japanese Journal of Clinical Laboratory Automation, 12(4), page 78, 1987. Such analysis machines dilute all samples considerably for the electrochemical analysis, but the additional preliminary dilution of a urine sample leads to very low values of sodium and chloride ions, which then become difficult to measure. Furthermore, if the preliminary dilution is an additional step performed by the operator, this is inconvenient. If the machine performs the additional dilution, the machine must be larger and more complicated.

Another document describing analysis of serum using an ion selective electrode is JP-A-60-73359 (1985), which describes a process in which the ion selective electrode is contacted first with a solution for calibration, i.e. an internal standard solution, then with the serum sample, and then with a cleaning solution which has characteristics similar to those of the internal standard solution. Measurements are taken for the calibration solution and the sample. Attention is also drawn to U.S. Pat. No. 4,680,270 which describes the use of ion selective electrodes in the analysis of blood samples.

SUMMARY OF THE INVENTION

An object of the invention is to provide a solution to at least some of the problems discussed above, and in particular to provide a method and apparatus for electrochemical analysis which permits samples of two different types to be contacted with an electrochemical sensor in a mixed sequence.

A further object of the invention is to provide a method and apparatus for electrochemical analysis in which at least two types of samples are analyzed and in which a preliminary dilution step for one type of sample is avoided, and in which the need for priming can be reduced.

Yet another object of the invention is to improve the response time of the electrochemical sensor in electrochemical analysis, when samples of two different types are contacted with the sensor.

It is a further object of the invention to provide an electrochemical analysis apparatus of relatively small size, suitable for analyzing samples of two different types.

The present invention is characterized by the use of a standard or calibrating first fluid for the electrochemical sensor and additionally the use of a second fluid which is different from the standard fluid and is adapted to improve generally the response of the sensor to one of the types of sample being analyzed. When the samples of two different types are presented to the sensor in mixed sequence, this additional fluid is contacted with the sensor at least at each change in the sequence from a sample or samples of one type to a sample or samples of the second type. The function of the additional solution is to prepare or sensitize the sensor for the next sample in the sequence.

For example, if the concentration of an ion being measured by an ion selective electrode is generally much higher in a second type of sample than in a first type of sample, the additional fluid can be chosen to have a higher concentration of this ion than the standard first solution. Then the additional solution sensitizes the electrode to the higher ion concentration which is to be expected in the immediately following sample of the second type. It has been found that the response time of an ion selective electrode is shorter than expected for small concentration changes; this may be due to a saturation effect. Slow response is particularly a problem with aged electrodes. Therefore, the use of the additional solution which sensitizes the electrode can reduce the overall response time, since the electrode is subjected to two small concentration changes rather than one large one.

This additional solution for an ion selective electrode is herein called an electrode response improving solution, and may include other components, such as anions, which improve the response of the electrode to the immediately following sample or sequence of samples of the same type.

The invention thus enables samples of two different types to be presented in a mixed sequence to the sensor, without the need for preliminary dilution of one of them. The response time of the electrode to samples of one of the types is improved, and the apparatus is made simple by the avoidance of a dilution line.

According to the invention in one aspect, therefore, there is provided a method of electrochemical analysis comprising the steps of contacting fluid samples of first and second different types in a mixed sequence with an electrochemical sensor and contacting the sensor with a standard first fluid, in order to measure the values of an analytical item in the samples with reference to a standard value of the same analytical item in the standard first fluid. At each change in the sequence from the first sample type to the second sample type, the sensor is contacted with a second fluid having a value of the analytical item closer to the mean value of the analytical item in the second sample type than the value of the analytical item in the standard first fluid. The value of the analytical item in the second fluid is preferably at least twice or at most one half of said value of said analytical item in the standard first fluid.

Preferably the standard fluid is contacted with the sensor at least immediately prior to each contact of a sample of the first type with the sensor and after a predetermined number of consecutive contacts in said sequence of the samples of the second type with the sensor. This effects a re-biasing of the sensor output to the standard fluid after the consecutive samples of the second type.

Preferably the second fluid is contacted with the sensor immediately prior to the contact of each sample of the second type with the sensor.

By a mixed sequence is meant a sequence of the samples in which there are at least two changes of type of sample in the sequence. The sequence of samples may thus be unplanned or random.

The invention further provides a method of electrochemical analysis comprising the steps of:

(i) contacting a standard first fluid having a fixed value of an analytical item with an electrochemical sensor at least once to obtain at least one output signal from the sensor;

(ii) contacting a plurality of fluid samples of two different types with the sensor in a mixed sequence to obtain respective output signals corresponding to the values of the analytical item in the samples;

(iii) at each change in the sequence from a sample of a first one of the types to a sample of a second one of the types, contacting a second fluid having a fixed value of the analytical item different from that of the standard first fluid with the sensor; and (iv) comparing the output signals for the samples with the output signal or signals for the standard first fluid.

Preferably, each sample and at least one of the standard first fluid and the second fluid are conveyed from storage containers towards said sensor by pipetting means.

In another aspect, an apparatus for electrochemical analysis according to the invention has (a) an electrochemical sensor;
(b) storage means for a first fluid;
(c) storage means for a second fluid;
(d) means for contacting the sensor with a mixed sequence of samples of two different sample types and with the first and second fluids to measure the value of an analytical item in each sample relative to the value thereof in the first fluid; and
(e) control means for the contacting means, arranged to cause contact of the second fluid with the sensor immediately prior to selected samples in the sequence and arranged to select the selected samples in dependence of the type of each sample and the type of the preceding sample in the sequence.

An apparatus for electrochemical analysis of blood serum and urine in accordance with the invention has (a) an electrochemical sensor including at least one ion selective electrode for sensing an ionic activity in blood serum and urine samples;
(b) storage means for an internal standard solution;
(c) storage means for an electrode response improving solution;
(d) means for contacting the sensor with a mixed sequence of blood serum samples and urine samples and with the internal standard solution and the electrode response improving solution;
(e) means for detecting and comparing outputs of the sensor when contacted by the solutions and the samples, in order to measure the ionic activity in each sample relative to the corresponding ionic activity of the internal standard solution; and
(f) control means for the contacting means arranged to cause contact of the electrode response improving solution with the sensor immediately prior to contact with the sensor of each urine sample in said sequence.

Preferably, the electrode response improving solution is an aqueous solution containing the following ions in the following concentrations:

| | |
|---|---|
| $Na^+$ | 80–120 |
| $K^+$ | 15–30 |
| $Cl^-$ | 60–100 |
| $HCO_3^-$ | 5–15 |
| $H_2PO_3^-$ | 5–15 |
| $SO_4^=$ | 5–15 |

Preferably this solution is free of urea and protein, and preferably its total concentration of ions is not more than 600 mmol/l.

The invention further provides an aqueous solution suitable for use in quantitative analysis of urine, containing the following ions in the following concentrations (mmol/l):

| | |
|---|---|
| $Na^+$ | 80–120 |
| $K^+$ | 15–30 |
| $Cl^-$ | 60–100 |

| | |
|---|---|
| $HCO_3^-$ | 5–15 |
| $H_2PO_3^-$ | 5–15 |
| $SO_4^=$ | 5–15 | and free of urea and protein, the total concentration of all ions being not more than 600 mmol/l.

BRIEF DESCRIPTION OF THE DRAWINGS

Embodiments of the invention will now be described by way of non-limitative example with reference to the accompanying drawings, in which.

DESCRIPTION OF THE PREFERRED EMBODIMENTS

Figure 1A:
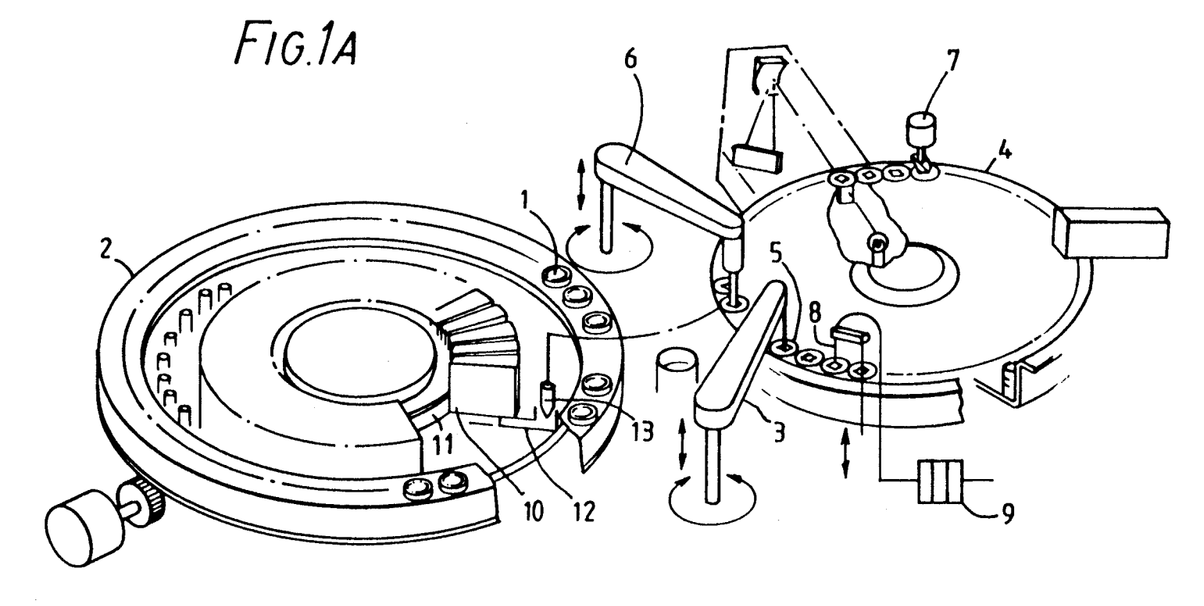
FIG. 1(A) is a perspective overhead view of an apparatus for electrochemical analysis according to the present invention.

FIG. 1(A) shows diagrammatically an apparatus for electrochemical analysis according to the present invention. An apparatus of this general type, for handling samples and reagents, is known in the medical analysis field and general aspects of construction and control of it do not need to be described. Attention is drawn, for example, to Hitachi's Blood Chemistry Analyzer 7150.

As shown in FIG. 1(A), samples which are to be measured are in sample vessels 1 on a rotatable sample disk 2. These samples are sucked sequentially in prescribed quantities by a rotatable sample pipette 3 and discharged into reaction vessels 5 which are arranged on a reaction line on a rotatable reaction disk 4 and kept at a temperature of 37° C. To each of these reaction vessels 5, a diluting solution is added by a rotatable reagent pipette 6 to dilute the sample 31 times, and the solution thus obtained is agitated by a mixer 7 and then sucked into an ion selective electrode element 9 by a sipper nozzle 8. The diluting solution is held in a reagent bottle 10 arranged on a reagent disk 11, the reagent bottle 10 and having a U-shaped reagent outlet 12. This dilution is standard for all samples.

Figure 1B:
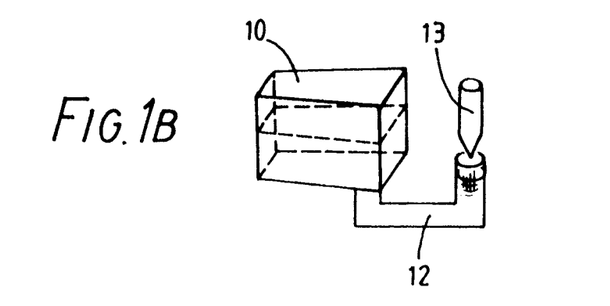
FIG. 1(B) is an enlarged view of a reagent bottle, a reagent holder and a reagent nozzle of the apparatus of FIG. 1(A)

The reagent outlet 12 is shown in the enlarged view of FIG. 1(B) and it extends to just under one location of a reagent nozzle 13 of the pipette 6. Inside the reagent bottle 10 of which the top is closed hermetically, a so-called Torricellian vacuum is formed. Therefore the reagent does not flow out, and only the portion sucked by the reagent nozzle 13 is supplemented automatically to the reagent outlet 12. The reagent pipette 6 thus sucks a prescribed quantity of diluting solution and discharges the same into the reaction vessel 5.

Since the diluting solution is supplied to the reaction vessel 5 by the reagent pipette 6 without using a long tube as in the prior art, a priming operation with the diluting solution flowing through a long passage is dispensed with, and consequently large quantities of the reagent can be saved.

Besides, the reagent, which in the prior art is usually supplied from a tank installed at a separate position, can be supplied from the reagent bottles arranged on the reagent disk 11 disposed within the periphery of the sample disk 2, and therefore the apparatus is reduced in size.

Figure 2:
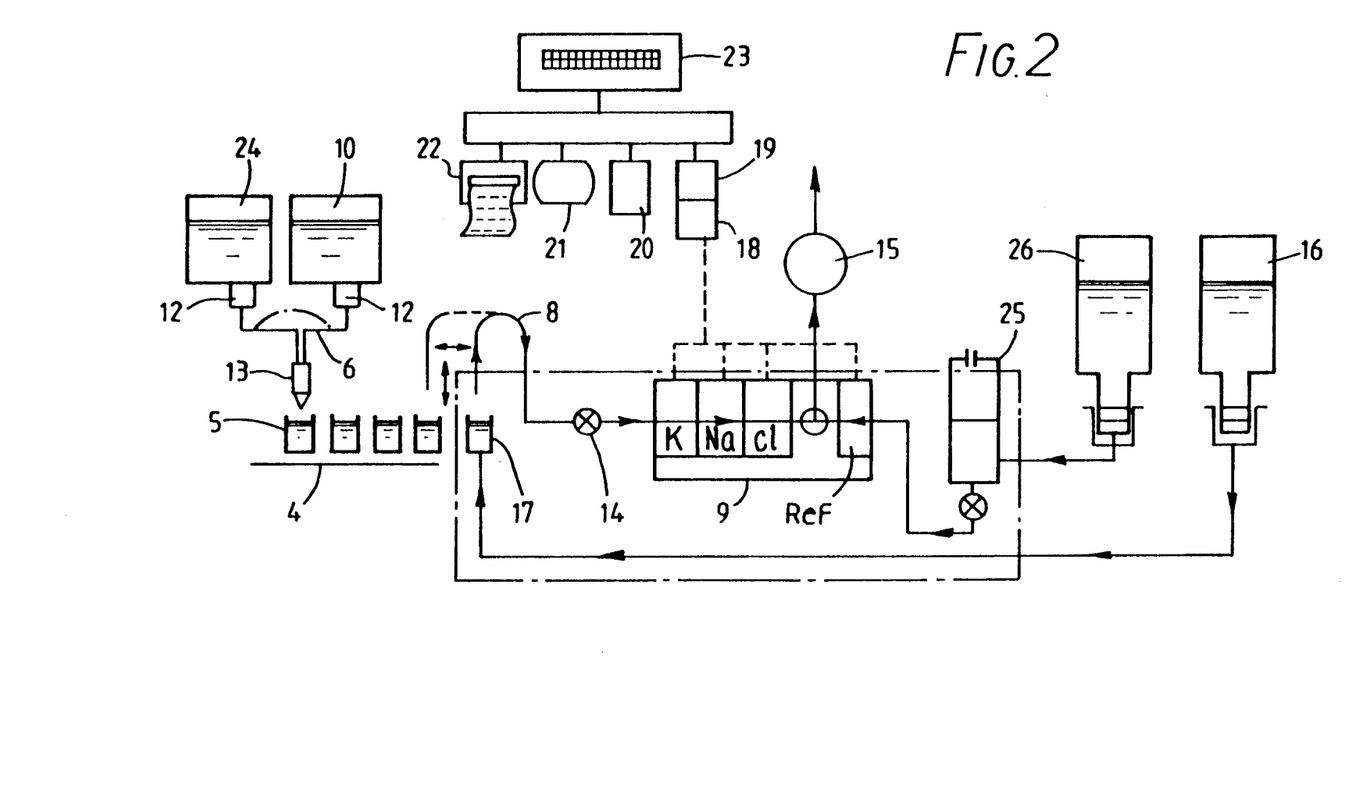
FIG. 2 is a diagrammatic illustration of liquid flow paths in the apparatus of FIG. 1(A)

In FIG. 2 showing flow paths of an electrolyte, the reagent, the internal standard solution (ISS), the electrode response improving solution (ERIS) etc. in the apparatus of FIG. 1, there are indicated the reaction vessels 5, the reagent pipette 6, the sipper nozzle 8, the ion selective electrode element 9, one of the reagent bottles 10 holding the reagents, the reagent outlet 12 shown by FIG. 1(B), the reagent nozzle 13, a solenoid valve 14 between the sipper nozzle 8 and the electrode element 9, a pump 15 for sucking each solution through the electrode element 9, a bottle 16 for the internal standard solution for serum (ISS), a vessel 17 for this internal standard solution supplied by the bottle 16 and also accessible by the sipper nozzle 8, an amplifier 18 for amplifying a signal from the ion selective electrode element 9, an A/D converter 19, a central processing unit (CPU) 20 for processing and judging data obtained from the ion selective electrode element 9 while controlling the operation of the whole apparatus, a display device 21 such as a cathode ray tube (CRT), a printer 22 printing the results of measurement etc., an information input device 23 in the form of a keyboard, a particular reagent bottle 24 introduced in accordance with the present invention, a deaerator tank 25, and a bottle 26 supplying a comparison solution for the measuring electrodes which is used when the whole apparatus is calibrated.

The reagent bottle 24 contains the electrode response improving solution (ERIS), whose nature and function is described below. The electrode element 9 consists of three ion selective electrodes, for $Na^+$, $K^+$ and $Cl^-$ respectively, through which each solution is passed in series, and a reference electrode. Such electrodes are known and are available from Hitachi, Ltd., for example.

Measurement is executed in the following way in the present embodiment. After the apparatus is put in a standby state, first, calibration solutions of known concentration (a standard LOW solution (STD LOW), a standard HIGH solution (STD HIGH)), for the electrodes are put in the reaction vessels 5, the diluting solution is added to each of them by the reagent pipette 6, and agitation is conducted by the mixer 7. The solution thus agitated is sucked to the ion selective electrode element 9 through the sipper nozzle 8 and the solenoid valve 14. After the solution has remained in the element 9 for several seconds, e.g. 20 seconds, the solenoid valve 14 is closed and the solution is sucked by the pump 15 and discharged to a waste solution tank not shown in the figure. Next, the internal standard solution for serum (ISS), the "standard first fluid," is sucked from the vessel 17 for the internal standard solution directly into the ion selective electrode element 9 by the sipper nozzle 8 after each measurement of a specimen of the aforesaid calibration solutions, and is measured by the electrodes and discharged by the pump 15 in the same way.

These operations are repeated in sequence three times for each of the STD LOW and the STD HIGH solutions, the electromotive force of each measured sample solution is processed by the CPU 20, and the slope value of each ion selective electrode of the element 9, i.e. the sensitivity thereof, and the concentration of the internal standard solution are calculated therefrom.

In the actual measurement of samples, the sample numbers and the types of samples (serum, urine or others) and their sequence are input beforehand by using the keyboard 23. The sequence of measurement of the types of sample is determined. Each of the samples after dilution is thereby sipped from a vessel 5 by the sipper nozzle 8, held in the electrodes for a short period, e.g. 20 seconds, and discharged.

FIGS. 3 to 6 illustrate sequences of operation of the apparatus of FIGS. 1 and 2. In each of FIGS. 3 to 6, the solutions passed through the element 9 are indicated at the left. The level of the line in the Figure indicates which of the solutions is passed at any given time. The symbols $M_1$, $M_2$ etc. indicate when measurements of the electrode emf are made.

Figure 3:
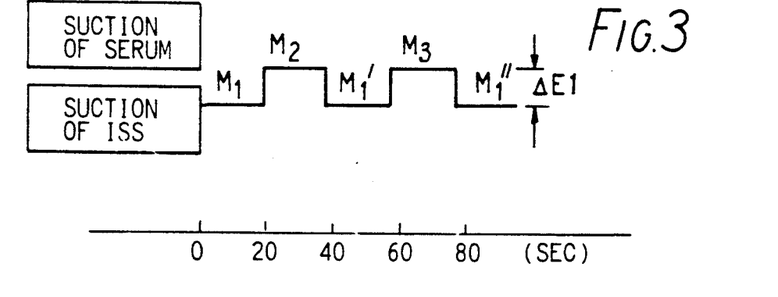
FIG. 3 is a diagram showing a measuring sequence for successive measurements of serum samples.

For successive measurements of serum only, the sequence of the suction and measurement of the internal standard solution for serum and the serum samples is executed as shown in FIG. 3. The result of measurement of each sample is obtained, for the first sample of serum, as a difference $\Delta E_1$ in the electromotive force between the measurement $M_2$ of the serum sample and the measurement $M_1'$ of the internal standard solution immediately after the measurement of the serum. If desired, the measurement for the internal standard solution just before the measurement of the serum and the measurement of the internal standard solution just after the measurement of the serum are compared in relation to the level measurement of the serum, a carry-over correction is executed to check the measurement, and the result is calculated accordingly.

Figure 4:
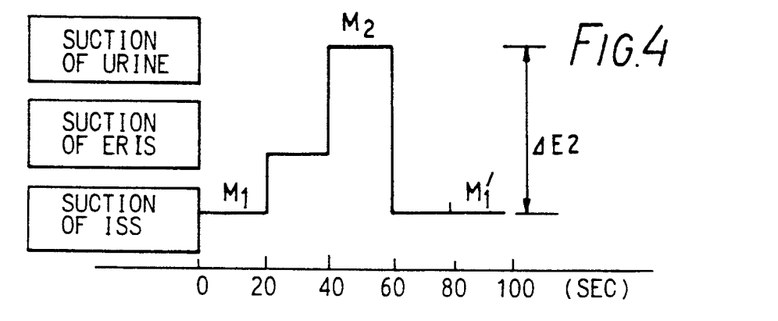
FIG. 4 is a diagram showing a measuring sequence for successive measurements of urine samples.

Next as FIG. 4 shows, in the measurement of a single urine sample, the sequence of (i) the suction and measurement of the internal standard solution for serum (ISS), (ii) suction of the electrode response improving solution (the "second fluid") for urine (ERIS), (iii) suction and measurement of the urine sample and (iv) a double portion suction of the internal standard solution for serum is executed. In this case, a difference $\Delta E_2$ in the electromotive force between the measurement $M_2$ for the urine sample and the measurement $M_1'$ for the second portion of the internal standard solution for serum after the measurement of the urine sample is used. Since the accuracy of response of the electrode is secured herein by using the electrode response improving solution, the result is calculated without conducting any carryover correction in respect of the internal standard solution.

The electrode response improving solution used in the present invention has a typical concentration of the ions $Na^+$, $K^+$ and $Cl^-$ within the range of normal values for these ions in urine, preferably close to the mean values for urine samples, and it is led to the ion selective electrode element 9 after the suction of the internal standard solution for serum so that the electrode response can be matched to the level of the following urine sample sufficiently. The electrode response improving solution for urine is discharged into the reaction vessel 5 from the reagent bottle 24 held on the reagent disk 11 through the reagent nozzle 13 of the reagent pipette 6, and thereafter it is sucked directly into the element 9 by the sipper nozzle 8 and then discharged to the waste solution tank in the same way as the other solutions.

Since urine has a considerable difference in level of concentration of $K^+$ ions, in particular, from the internal standard solution for serum, according to the present method, the level difference from the internal standard solution for serum is lessened and therefore an accurate result can be obtained without executing a priming operation. This leads also to the saving of the reagents.

Figure 5:
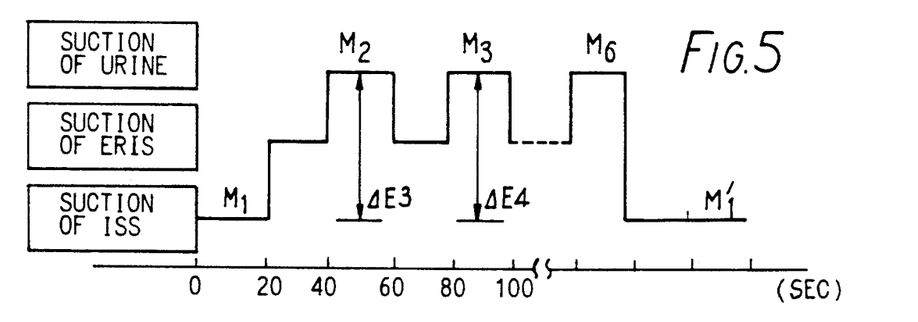
FIG. 5 is a diagram showing a measuring sequence of successive measurements of five or more urine samples.

The successive measurement of urine samples, e.g. the successive measurement of five samples or more, is shown in FIG. 5. The electrode response improving solution for urine is sucked without the suction of the internal standard solution for serum between urine samples. After a predetermined number of urine samples, which number is greater than one, and in the present embodiment is five, the internal standard solution for serum is again sucked in a double portion. The internal standard solution for serum is thus sucked and measured twice for every five specimens of urine, and differences ($\Delta E_3$, $\Delta E_4$, etc.) in the electromotive force between the measurement $M_1'$ of the ISS and the measurement $M_2$, $M_3$ etc. of the urine samples are outputted as the results. The electrode response improving solution for urine is used, so to speak, as a sub-standard solution in this case, and thereby a reduction in the measuring time is achieved.

Figure 6:
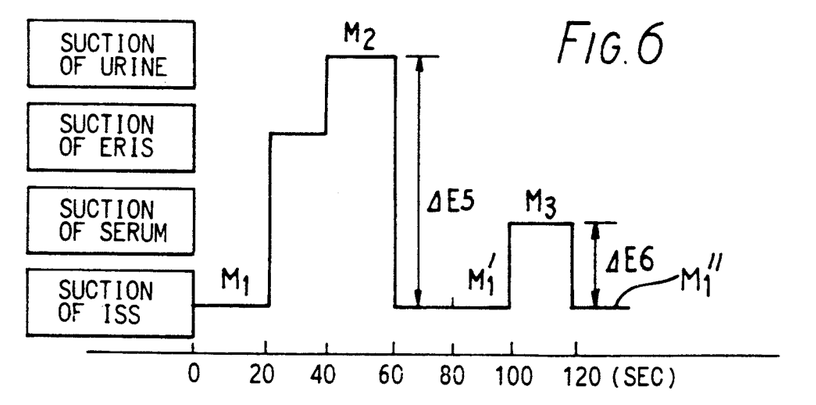
FIG. 6 is a diagram showing a measuring sequence of serum and urine samples in a mixed order.

Moreover, in the measurement of urine and serum samples in a mixed sequence, the sequence of the suction and measurement of the ISS, the ERIS, the urine samples and the serum samples is executed as illustrated by FIG. 6.

As to the urine, a difference $\Delta E_5$ in the electromotive force between the measurement of the internal standard solution after the measurement $M_2$ of the urine sample and the measurement of the urine sample itself is adopted as the result of measurement, while as to the serum, a difference $\Delta E_6$ in the electromotive force between the measurement $M_1''$ of the internal standard solution for serum just after the measurement of the serum and the measurement $M_2$ of the serum is adopted as the result of measurement. As for the correction of the carry-over, the same steps as in the case of successive measurement are taken for both the urine and the serum, if desired.

Assuming that the rate of suction of a sample is 300 $\mu$l in 8 sec., the speed of treatment is 90 specimens/hour in the successive measurement of the serum and 45 specimens/hour in the successive measurement of the urine. The result of each measurement is printed by the printer 22, with a discriminant expression discriminating the type of sample (serum, urine or others) marked simultaneously.

Table 1 below gives the ranges of normal values of the concentrations of the three measured ions, the concentration of those ions in the internal standard solution for serum and the electrode response improving solution for urine, and thirdly the desired measurement assurance range, i.e. desired range of accurate measurement.

The ranges of normal values of urine and the measurement assurance range thereof are wider than those of serum and the mean value for potassium ions is different by three to five times in particular, from that of the serum as shown in the Table 1 below. Therefore, the concentration of the electrode response improving solution is set in proximity to the central value of the range of the normal values for urine in the present embodiment.

Table 2 gives the compositions of the internal standard solution for serum and the electrode response improving solution for urine. The $Na^+$ and $Cl^-$ concentrations do not differ greatly, but the $K^+$ concentration differs by four times.

Figure 8A:
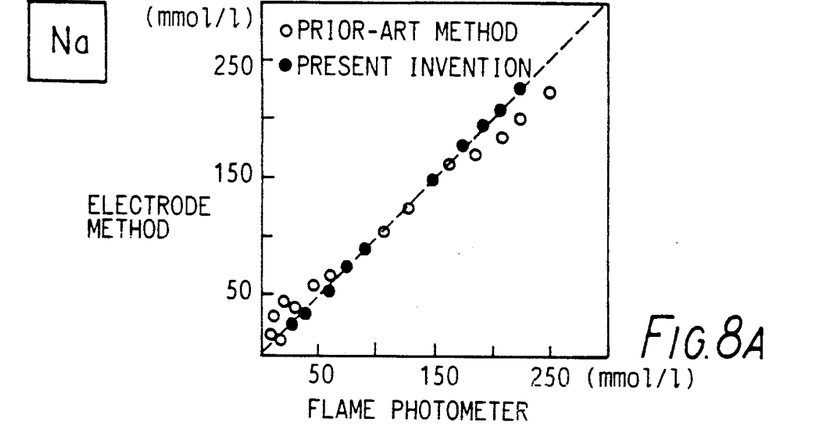
FIGS. 8A, 8B and 8C are three graphs showing correlations between a prior-art method, a method embodying the present invention and measuring methods serving as references.
Figure 8B:
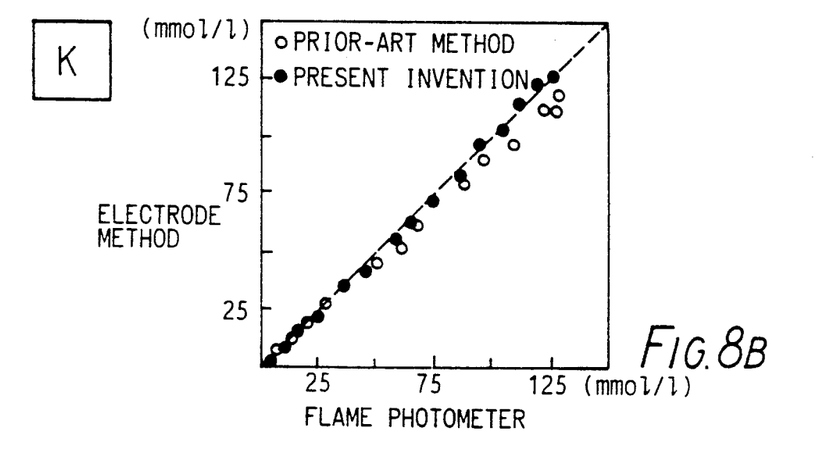
Figure 8C:
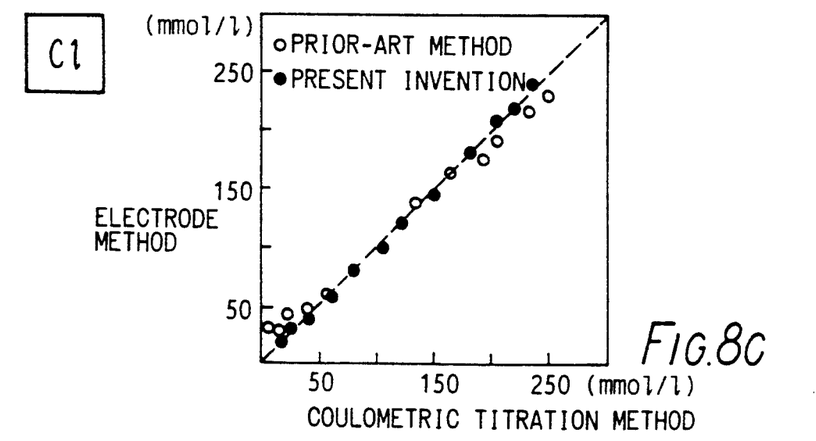

In the composition of the electrode response improving solution there are included phosphate anions ($H_2PO_4^-$), bicarbonate ions ($HCO_3^-$), sulfate ions ($SO_4^=$), etc. being anions contained in large quantities in urine as well as the ions of sodium, potassium and chloride as shown in Table 2, so as to make it approximate to a urine matrix. This further improves the response of the ion selective electrodes to the urine samples.

of the ion selective electrode method are taken for the vertical axis. Samples are measured by both methods, and the results are plotted. Open circles represent the results obtained with the prior-art method of using the ion selective electrodes wherein preliminary dilution in two to four times is made by using distilled water and no ERIS is used, while filled circles represent the results according to the present embodiment. The closeness of the results to the results obtained by the reference is given by the closeness of the plotted points to the line $x=y$.

It is seen from these diagrams that the values for sodium and chloride ions are positioned substantially on the straight line of $x=y$ for the present embodiment while they tend to be somewhat higher at a low concentration region and somewhat lower at a high concentration area for the prior-art method. As for potassium the values are good like those of sodium and chloride in the present embodiment, while they tend to be lower in the high concentration region in the prior art method.

TABLE 1

| Item | Serum (mmol/l) | | | Urine (mmol/l) | | |
|---|---|---|---|---|---|---|
| | Range of normal values | Concentration of internal standard solution | Measurement assurance range | Range of normal values | Electrode response improving solution for urine | Measurement assurance range |
| $Na^+$ | 138–149 | 140 | 80–180 | 65–130 | 100 | 10–350 |
| $K^+$ | 3.7–4.9 | 5.0 | 1.5–10 | 13–25 | 20 | 1–100 |
| $Cl^-$ | 99–108 | 100 | 60–120 | 55–120 | 80 | 10–250 |

TABLE 2

| | Internal standard solution for serum (mmol/l) | | Electrode response improving solution for urine (mmol/l) | |
|---|---|---|---|---|
| Composition | NaCl | 100 | NaCl | 70, KCl 10 |
| | $KH_2PO_4$ | 5.0 | $NaHCO_3$ | 10, $KH_2PO_4$ 10 |
| | $NaHCO_3$ | 40 | $Na_2SO_4$ | 10 |

Figure 7:
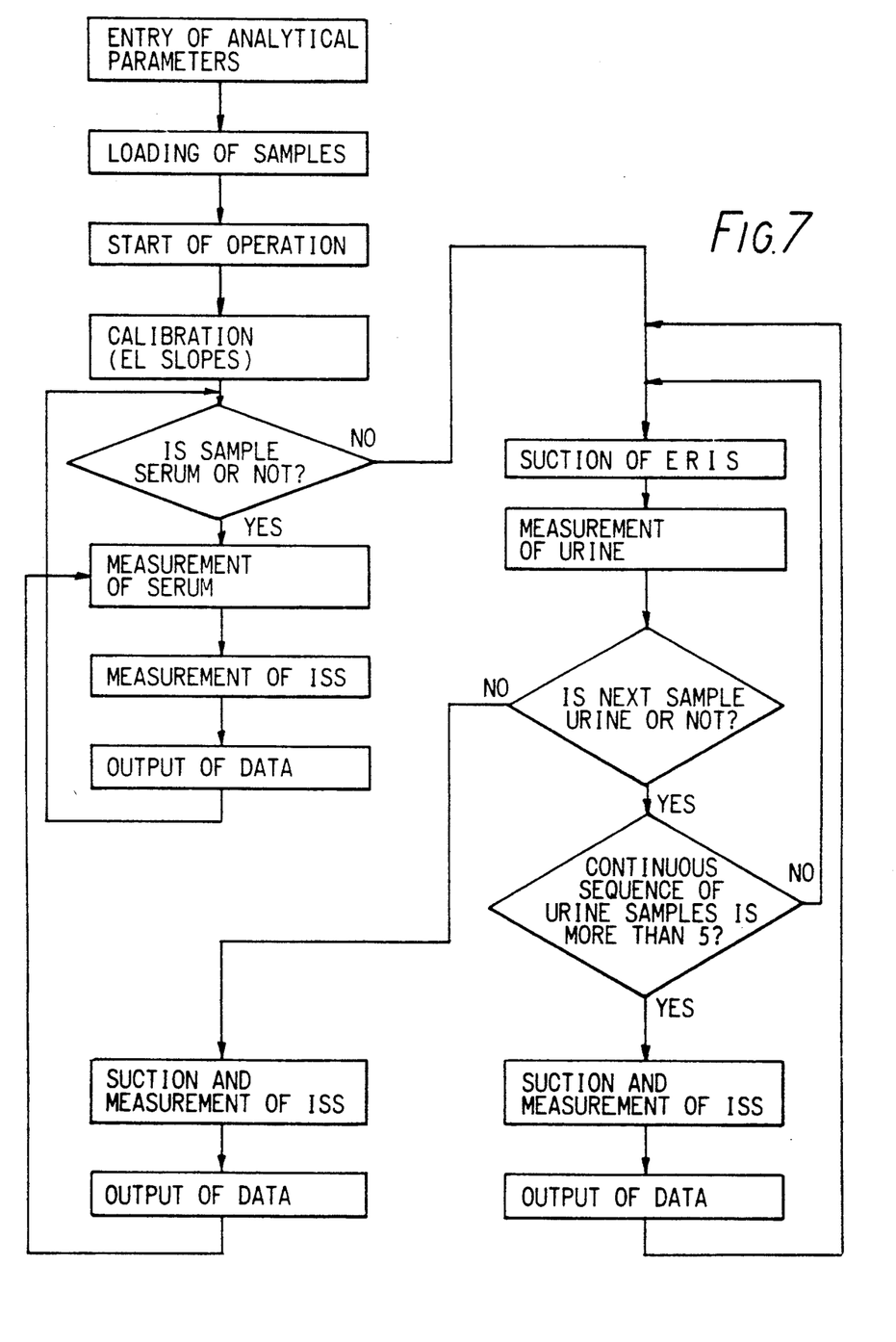
FIG. 7 is a logic diagram for a method of analysis according to the invention, such as that of FIG. 6.

FIG. 7 is a logic diagram for the method of analysis employed in the apparatus of FIGS. 1 and 2, using the principle of FIG. 6.

In FIG. 7 the initial items are identified as entry of analytical parameters and loading of samples. Before the analysis of a large number of samples begins, it is necessary to enter the parameters of the sodium, potassium and chloride ion concentrations in the standard solutions used for calibration, and to enter the sequence and types of the samples to be analyzed, i.e. serum or urine. After the start of the operation, the first step is the calibration of the ion selective electrodes as already described, to obtain response slopes of the ion selective electrodes. Thereafter the routine sample analysis begins. First the control means ascertains whether the next sample to be analyzed is serum or urine. The subsequent steps are set out in FIG. 7, and depend upon the sequence of samples. Immediately preceding the measurement of each urine sample, the ERIS is sucked through the electrodes. Note in particular that if there is a continuous sequence of urine samples of more than five, after five urine samples there is suction and measurement of the internal standard solution, prior to the measurement of the next urine sample.

Examples of the results of measurement according to the present embodiment are shown in FIG. 8. This figure shows scatter diagrams relating to sodium, potassium and chloride ions, wherein the measured results of a standard reference method (flame photometry for $Na^+$ and $K^+$, and coulometric titration method for $Cl^-$) are taken for the horizontal axis, while the results According to the present embodiment, accordingly, accurate results of analysis can be obtained quickly without providing any special diluting measures.

What is claimed is:

1. A method of electrochemical analysis, comprising the steps of:
   (i) contacting a first fluid having a fixed value of an analytical item with an electrochemical sensor at least once to obtain at least one output signal from the electrochemical sensor;
   (ii) contacting first and second pluralities of fluid samples with said electrochemical sensor in a mixed sequence to obtain respective output signals corresponding to the values of said analytical item in said samples, said first and second pluralities having different respective analytical characteristics;
   (iii) at each change in said sequence from a sample of said first plurality to a sample of said second plurality, contacting a second fluid having a value of said analytical item different from that of the first fluid with said electrochemical sensor; and
   (iv) comparing said output signals of said samples with said at least one output signal for said first fluid.

2. A method according to claim 1, wherein said analytical item is ionic activity.

3. A method according to claim 1, wherein said electrochemical sensor is an ion selective electrode.

4. A method according to claim 1, wherein said first and second fluid sample pluralities are blood serum and urine, respectively.

5. A method according to claim 1, wherein said value of said analytical item in said second fluid is at least twice or at most one half of said value of said analytical item in said first fluid.

6. A method according to claim 1, wherein each said sample and at least one of said first fluid and said second fluid are conveyed from storage containers towards said electrochemical sensor by pipetting means.

7. An apparatus for electrochemical analysis, comprising:
(a) an electrochemical sensor;
(b) storage means for storing a first fluid;
(c) storage means for storing a second fluid;
(d) means for contacting said electrochemical sensor with a mixed sequence of first and second pluralities of samples and with said first and second fluids to measure the value of an analytical item in each said sample relative to the value thereof in said first fluid, said first and second pluralities having different respective analytical characteristics;
(e) control means for controlling said contacting means, said control means being arranged to cause contact of said second fluid with said electrochemical sensor immediately prior to selected samples in said sequence and arranged to select said selected samples in dependence on the plurality to which the selected sample belongs and on the plurality to which the preceding sample in the sequence belongs.

8. An apparatus according to claim 7, wherein said analytical item is ionic activity and said electrochemical sensor is an ionic selective electrode.

9. An apparatus according to claim 7, further comprising a plurality of containers for said samples, and pipetting means for conveying said samples from said containers and at least one of said first and second fluids from a respective storage means towards said electrochemical sensor.

10. An apparatus for electrochemical analysis of blood serum and urine, comprising:
(a) an electrochemical sensor including at least one ion selective electrode for sensing ionic activity in blood serum and urine samples;
(b) storage means for storing an internal standard solution;
(c) storage means for storing an electrode response improving solution;
(d) means for contacting said electrochemical sensor with a mixed sequence of blood serum samples and urine samples, and with said internal standard solution and said electrode response improving solution;
(e) means for detecting and comparing outputs of said electrochemical sensor when contacted by said solutions and said samples, in order to measure the ionic activity in each said sample relative to the corresponding ionic activity of said internal standard solution; and
(f) control means for controlling said contacting means, said control means being arranged to cause contact of said electrode response improving solution with said electrochemical sensor immediately prior to contact with said electrochemical sensor of each said urine sample in said sequence.

11. An apparatus according to claim 10, wherein said electrode response improving solution is an aqueous solution containing the following ions in the following concentration (mmol/l):

| | |
|---|---|
| $Na^+$ | 80–120 |
| $K^+$ | 15–30 |
| $Cl^-$ | 60–100 |
| $HCO_3^-$ | 5–15 |
| $H^2PO_3^-$ | 5–15 |
| $SO_4^=$ | 5–15. |

12. An apparatus according to claim 11, wherein said electrode response improving solution is free of urea and protein.

13. An apparatus according to claim 11, wherein the total concentration of ions in said electrode response improving solution is not more than 600 mmol/l.

14. An apparatus for electrochemical analysis of blood serum and urine samples, comprising:
(a) an electrochemical sensor;
(b) storage means for storing a standard solution;
(c) storage means for storing an electrode response improving solution;
(d) means for contacting said electrochemical sensor with a group of blood serum samples and a group of urine samples in a sequence in which said blood serum samples and said urine samples are commonly arranged, and for contacting said electrochemical sensor with said standard solution and said electrode response improving solution to measure ionic activity in each said sample relative to the value of said ionic activity in said standard solution;
(e) control means for controlling said contacting means, said control means being arranged to cause contact of said electrode response improving solution with said electrochemical sensor immediately prior to contact of each sample of one of said groups with said electrochemical sensor, and to cause contact of said standard solution with said electrochemical sensor immediately prior to contact of each sample of the other of said groups with said electrochemical sensor; and
(f) said electrode response improving solution having a value of said ionic activity closer to the mean value of said ionic activity in said one of said group of samples than to said value of said ionic activity in said standard solution.

15. An apparatus according to claim 14, wherein said control means is adapted and arranged to cause contact of said standard solution with said electrochemical sensor after a predetermined number of consecutive contacts in said sequence of samples of said one of said groups with said electrochemical sensor.

* * * * *